United States Patent [19]

Evenson et al.

[11] Patent Number: 4,559,309
[45] Date of Patent: Dec. 17, 1985

[54] FLOW CYTOMETRY-FLUORESCENCE MEASUREMENTS FOR CHARACTERIZING SPERM

[75] Inventors: Donald P. Evenson, Brookings, S. Dak.; Zbigniew Darzynkiewicz, Cheppaque, N.Y.

[73] Assignee: Memorial Sloan Kettering Cancer Center, New York, N.Y.

[21] Appl. No.: 413,862

[22] Filed: Sep. 1, 1982

[51] Int. Cl.⁴ ..................... G01N 21/64; G01N 33/52
[52] U.S. Cl. .................................. 436/63; 250/461.2; 436/94; 436/172
[58] Field of Search ........................ 436/63, 94, 172; 250/461.2; 424/3

[56] References Cited

U.S. PATENT DOCUMENTS 3,657,537 4/1972 Wheeless, Jr. et al. .......... 250/461.2
3,684,377 8/1972 Adams et al. .......................... 356/36
3,899,297 8/1975 Hirschfeld ............................ 436/172

OTHER PUBLICATIONS

Evenson et al., Science, vol. 210, No. 4474, Dec. 1980, pp. 1131-1133.
Clausen et al., 5th Annual Workshop on the Testis, Geilo, Norway, Apr. 1978, International Journal of Andrology, Supplement 2(1978), pp. 513-521.
Johnson et al., Proc. Natl. Acad. Sci., vol. 77, No. 2, Feb. 1980, pp. 990-994.
Darzynkiewicz et al., Proc. Natl. Acad. Sci., vol. 78, No. 4, Apr. 1981, pp. 2383-2387.
Cohen et al., Nature, vol. 290, Apr. 1981, pp. 593-595.
Shapiro et al., Proc. Natl. Acad. Sci., vol. 76, No. 11, Nov. 1979, pp. 5728-5730.
Taylor, Chemical Abstracts, vol. 93, 1980, No. 93:163918q.
Clausen et al., Chemical Abstracts, vol. 89, 1978, No. 89:175906q.
Nicolini et al., Chemical Abstracts, vol. 90, 1979, No. 90:148008n.

Primary Examiner—Arnold Turk
Attorney, Agent, or Firm—Felfe & Lynch

[57] ABSTRACT

A process for characterizing sperm motility and viability by staining a sperm sample with Rhodamine 123 and ethidium bromide, and simultaneously measuring the sperm fluorescence emissions at green frequencies 515-575 nm and at red frequencies 600-650 nm, the green counts being correlated with sperm motility and the red counts being correlated with putative dying or dead cells. Additionally, a sample of sperm can be characterized as to type and normality by staining a sample of sperm with acridine orange and simultaneously measuring the sperm fluorescence emissions at green frequencies 515-575 nm and at red frequencies 600-650 nm.

2 Claims, 2 Drawing Figures

EB/R123 STAINED SEMEN CELLS

EB/R123 STAINED SEMEN CELLS

FLOW CYTOMETRY-FLUORESCENCE MEASUREMENTS FOR CHARACTERIZING SPERM

BACKGROUND

The present invention provides a simple, rapid procedure for characterizing sperm using flow cytometry measuring techniques coupled with staining by various dyes.

Characterizing motility, viability, and sperm morphology can provide useful information not only with respect to reproduction but also as an early warning monitor of excessive invasion by dangerous agents (including radiation) into the body. The mammalian testis is a target organ for chemical toxins in the work place and environment. In addition, radiation from various natural and man made sources can cause degenerative effects. The adverse effects can include a reduction in the number of testicular spermatids, secondary spermatocytes, and sperm—and in even more dramatic cases, a loss of spermatogonia (N.Engl. J. Med. 298:234(1978); Lancet 2:1259 (1977)). In the area of cancer chemotherapy, numerous studies have demonstrated significant, acute and long term gonadal dysfunction in patients receiving chemotherapy, although recovery has been found possible. Recent studies (Science 215:643 (1982) have suggested that effects on reproduction and chromosomes may be the best indicators of exposure to chemicals.

The present invention provides a means whereby sperm may be characterized and thereby act as an indicator of invasions into the body by chemicals, diseases, etc.; as well as a rapid accurate method which may easily be applied in fertility clinics for diagnosis, counseling and prognosis purposes. The inventive method can also be applied for screening persons who may be in contact with excessive radiation as a medical, diagnostic tool e.g. uranium miners who may be in contact with very low level radiation for extended periods of time, making detection by other means impossible or extremely expensive.

Analysis of the effects of gonadal dysfunction by light microscopy, now presently employed, is semi-quantitative at best, and is quite subjective and time consuming. Furthermore, conventional staining procedures cannot easily distinguish between various cell types e.g. lymphocytes versus immature spermatids, if this can be accomplished at all. Furthermore, it is difficult, if not practically impossible, to distinguish variations of chromatin condensation by light microscopy usually employed in screening laboratories.

The present invention provides flow cytometry (FCM) methods with significant advantages over the usually applied prior art methods, for the analysis of semen (and testicular biopsies) including: (1) rapidity of measurement (1,000 cells per second); (2) unbiased selection of cells for measurement; (3) simultaneous multi-parameter measurements per cells; (4) objective criteria for classification defined by machine specifications; (5) statistical strengths; and (6) ease of classifying and differentially counting different cell types.

Flow cytometry has been applied in the analysis of sperm precursor cells (Cohn et al N.Engl. J. Med. 298: 234 (1978); DNA content of mature sperm (Gledhill et al in: Flow Cytometry and Sorting, Melamed et al (Eds.), John Wiley & Sons, N.Y. page 471 (1979)) and variations in sperm head shapes (Benaron et al Cytometry 2:344 (1982)) as dosimeters of mutagenic chemical exposure. Similarly, fine needle biopsies of human testis has been studied by flow cytometry of DNA content (Thouid et al Acta Pathol. Microbiol. Scand. 275: 175 (1981)). However no one has previously applied flow cytometry as in the present invention to characterize sperm.

SUMMARY

The present invention provides a method by which RNA and DNA content/chromatin condensation as well as cell fertility and motility can all be determined in rapid simple and precise manner using flow cytometry.

To quantitate RNA content and DNA content/chromatin condensation a fresh semen sample (1-6 hours post emission) or frozen sample (allowing samples to be accumulated and sent to a laboratory) is treated with a detergent solution, stained with acridine orange (AO) and measured by flow cytometry (FCM); approximately ten minutes are required to measure 5,000 cells per sample and analyze the data with computer assistance. The following can be learned from a single measurement: (a) the percentage of each cell type in semen inluding, (i) mature sperm, (ii) immature sperm precursor cells representing all stages of development from spermatogonia to mature sperm, (iii) somatic cells, e.g. leukocytes; (b) normality/abnormality of sperm nuclear chromatin condensation. These measurements can be correlated with cell types in testis biopsies identified by two parameter FCM measurements (RNA vs. DNA) using acridine orange as the fluorescent probe and measuring simultaneously the red and the green fluorescent values of each cell and storing in computer memory the integrated values for each cell.

Following a similar procedure sperm samples are also stained with Rhodamine 123 (Red) and ethidium bromide (green) and measured with flow cytometry techniques giving a measure of mitochondrial membrane potential which correlates with cell motility and cell viability.

Using the measurements generated by the inventive method, the fertility and health of the mammalian donor and the condition of the sperm, can be indexed.

DESCRIPTION

Figure 1:
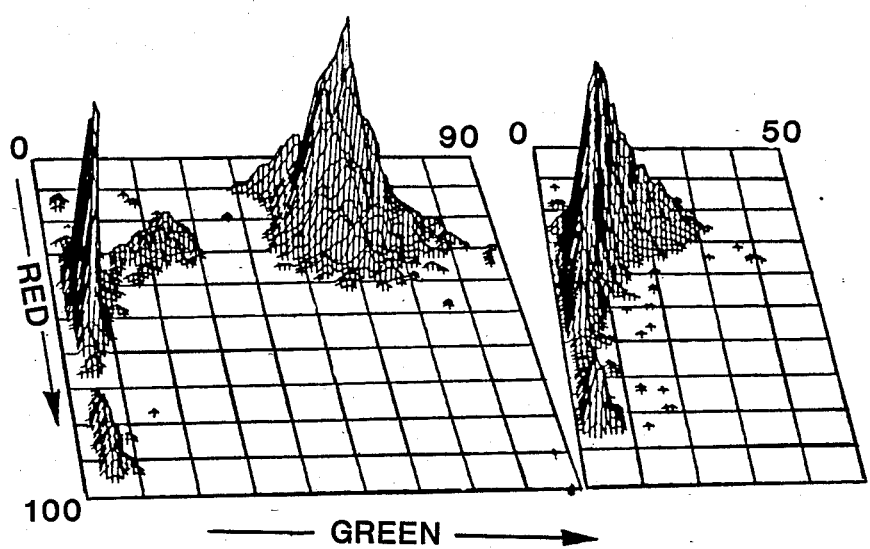
FIG. 1 shows a two parameter histogram demonstrating stainability of human sperm cells with rhodamine 123 and ethidium bromide.

Sperm can be indexed as to viability, motility, morphology/maturation and ratio of cell types using flow cytometry measurements of red and green cells stained with Rhodamine 123 (R123), ethidium bromide (EB) and acridine orange(AO).

Flow cytometry of sperm cells stained green with Rhodamine 123 (R123) and red with ethidium bromide (EB) provides a rapid, quantitative analysis of mitochondrial membrane potential (correlated here with cell motility) and cell viability. Staining green or red with acridine orange and applying flow cytometry measuring techniques results in measurements which can be correlated with (a) the percentage of each cell type in semen including, (i) mature sperm, (ii) immature sperm precursor cells representing all stages of development from spermatogonia to mature sperm, (iii) somatic cells e.g. leukocytes; (b) normality/abnormality of sperm nuclear chromatin condensation.

The staining specificity of R123 for mitochondria was described recently by Johnson et al. Proc. Natl. Acad. Sci. USA 77:990 and quantitated via flow cytometry by Darzynkiewiecz et al, Proc. Acad. Sci. USA 78:2383 and Cancer Research. After staining with R123, differences in fluorescence intensity between cells are believed due to a variable number of mitochondria per cell, Darzynkiewicz et al, Cancer Research 42:799, or a difference in mitochondrial membrane potential, Cohen et al, Nature 290:593 and Shapiro et al, Proc. Natl. Acad. Sci. USA 76:5728, both of which are related to the metabolic processes of the cell. Ethidium bromide is used as a counterstain to determine cell viability indicated by exclusion of the dye by living cells. Acridine orange staining can identify two parameters (DNA vs RNA) which can be correlated with cell types in testis biopsies.

The sperm in suspension, stained with AO, R 123 and EB, were measured individually in a flow cytometer at rates up to one thousand per second. The resulting data permits full characterization of sperm, accomplished quickly and easily. Thus, statistically significant populations were easily assayed, offering an advantage over the slower, semi-quantitative methods used currently for analyses of sperm motility and viability. Also the use of mitochondrial membrane potential as a mesurement of cell motility was not previously reported and the use of AO for cell morphology indexing is more sensitive than current light microscope techniques thereby giving more and/or better information.

EXPERIMENTAL

R123/EB Staining

A semen sample obtained from a normal individual of proven fertility was stained and measured at (A) 4 hours after collection, and (B) 30 hours after collection. The sample was kept at room temperature in a flat bottomed plastic jar. Prior to measurement, the semen was diluted to approximately $1-2 \times 10^6$ cells per ml in RPMI 1640 media (GIBCO, Grand Island, N.Y.) containing 10% fetal calf serum (GIBCO). Alternatively, samples were suspended and stained in phosphate buffered balanced salt solution (PBS) containing 1% (w/v) sucrose, with similar results.

The samples were stained with R123 (Eastman Organic Chemicals, Rochester, N.Y. laser dye purity) at 10 $\mu$g/ml final concentration for 10 mins; then the sperm were pelleted, resuspended in the same medium and counterstained with EB (10 $\mu$g/ml, Polysciences, Warrington, Pa.). A stock solution of R123 was made in distilled water (1 mg/ml) and diluted into the sample solution. All procedures were done at room temperature.

After 30-60 mins. the samples were analyzed in an FC 200 Cytofluorograf equipped with a 488 nm argon-ion laser (Ortho Diagnostic Instruments, Westwood, Mass.) interfaced to a Data General minicomputer. The green ($F_{530}$ at 515-575 nm) and red ($F_{600}$ measured in a band of 600-650 nm) fluorescence emissions were separated optically (filters) and measured by different photomultipliers; the integrated values of the respective pulses of each cell were recorded by the computer. The data were based on the measurement of 5,000 cells.

Sperm in suspension, stained with R123/EB as described above were observed by U.V. and light microscopy using a Leitz Orthoplan microscope fitted with epifluorescent illumination (485 nm excitation and 530 nm emission filters). The green fluorescence of R123 was restricted to the midpiece containing the mitochondria, and the red fluorescence of EB staining putative dying or dead cells was located in the sperm head. Bright green fluorescence correlated with fast motility. Bright red and green fluorescence were mutually exclusive. However, some cells did exhibit both pale red and pale green fluorescence localized in the head and midpiece respectively. These and other data indicated that impaired or dying cells stained with R123 under nonequilibrium conditions lose green fluorescence before, or as they begin to show red fluorescence. Somatic cells undergo a transient increase in uptake of R123 prior to cell death and lysis, Darzynkiewicz et al, *Cancer Research*, 42:799 not seen in dying sperm cells.

To quantitate RNA content and DNA content/chromatin condensation for each of many possible cell types and differentiation levels of the cells present in human semen, a fresh semen sample (1-6 hours post emission) or frozen sample (allowing samples to be accumulated and sent to a laboratory) was treated with a detergent solution, stained with acridine orange (AO) and measured by flow cytometry (FCM); approximately ten minutes are required to measure 5,000 cells per sample and analyze the data with computer assistance. The following can be learned from a single measurement: (a) the percentage of each cell type in semen including, (i) mature sperm, (ii) immature sperm precursor cells representing all stages of development from spermatogonia to mature sperm, (iii) somatic cells, e.g. leukocytes; (b) normality/abnormality of sperm nuclear chromatin condensation. These measurements were correlated with cell types in testis biopsies identified by two parameter FCM measurements (RNA vs. DNA) using acridine orange as the fluorescent probe being available for AO intercalation and any increase in red/red pulse green fluorescence is due to AO interaction with single strand DNA.

AO Staining

Semen was obtained from patients who were concerned about their fertility status including patients whose inquiry was related to cancer or its therapy. Control semen samples were obtained from healthy volunteers who have fathered at least two children and have been free of any urogenital problems between the last conception and donation of sample.

Semen samples were collected in the clinic by masturbation into a plastic specimen container. After a minimum of one-half hour to allow for liquification to occur, the samples were analyzed.

Samples that could be analyzed within 1-6 hours were maintained at room temperature. Routine analyses of semen volume and pH, sperm density, motility and morphology were done within several hours. For reasons of time, convenience or machine availability, samples were often admixed 1:1 with ultrapure glycerol and stored in a standard refrigerator freezer ($-20°$ C.) for periods ranging from overnight to a month of time. Longer term storage was at $-70°$ C.; such storage had no significant effect on the data. Glycerol: semen (1:1) mixtures kept at $-20°$ C. remain fluid so that small aliquots can be drawn off with a pipette. In our laboratory, control semen samples are kept in this manner for up to a month so that an aliquot can be easily drawn off to serve as a reference marker for FCM analysis of patient samples.

Severe oligospermic or near azoospermic samples are used directly, without dilution, whereas normal semen containing $100-200 \times 10^6$ cells per ml is diluted in Hank's balanced salt solution (HBSS) to an approximate concentration of $2 \times 10^6$ cells/ml. The dilution can be adjusted, if necessary, to achieve an acceptable flow rate of the cells through the FCM channel.

A 0.2 ml sample of semen or a semen dilution is mixed with 0.4 ml of a detergent solution consisting of 0.1% Triton X 100 (Sigma Chemical Co., St. Louis, Mo.) in 0.08N HCl, 0.15M NaCl; this step significantly reduces the viscosity of semen. Thirty seconds later, 1.2 ml of a solution containing 0.2M $Na_2HPO_4$-0.1M citric acid buffer (pH 6.0), 1 mM EDTA, 0.15M NaCl, and 6 μg AO/ml (chromatographically purified, Polysciences, Inc., Warrington, Pa.) is admixed with the sample as previously described (3). The stained sample is immediately introduced into the flow cytometer and measured within 1-3 minutes.

Pretreatment of cells with Triton X-100 at low pH renders the cells permeable to the dye while the nucleic acids remain insoluble under these conditions. Subsequent staining with AO in the presence of chelating agents (EDTA, citrate) results in denaturation of all cellular RNA, which stains metachromatically red dye to dye-base interactions (13), while native DNA intercalates the dye and stains orthochromatically green (14).

Fluorescence of individual cells was measured with a FC-200 Cytofluorograf (Ortho Diagnostic Instruments, Westwood, Mass.) interfaced to a Nova 1220 minicomputer (Data General Corp., Southboro, Mass.). The cells suspended in the dye solution are transported through the instrument at a rate of about 200 per second; however, in cases of very low sperm count, that rate may only be several cells per second. Fluorescence signals are generated within each stained cell as it passes through the focus of a 488 nm argon-ion laser beam. The red ($F_{600}$) and the green ($F_{530}$) fluorescence emission for each cell are differentiated by means of optical filters, recorded with separate photomultipliers, and the integrated values stored in the computer. The green pulse width, i.e. the time taken for a cell to pass through the laser beam was also recorded and used to distinguish single cells from cell doublets and to determine nuclear diameter (18). A total of 5,000 cells were recorded for each sample with the exception of "azoospermic semen" samples which contained fewer than 5,000 cells. Even in these cases meaningful data could be obtained with only several hundred cells.

FIG. 1 shows data on a single ejaculate of sperm cells obtained from a fertile male; sample A was measured 4 hours after collection and sample B at 30 hours. At 4 hr 70% of the sperm had a high level of R123 staining and 26% had a reduced level; 4% had a high level of EB staining indicating dead cells. Thirty hours after collection all cells had a reduced though variable level of R123 staining relative to sample A; 13% had a high level of motility in the 4 hr sample and a low level of motility in the 30 hr sample. This experiment was repeated with three different samples with similar results. Samples obtained from patients attending an infertility clinic and others undergoing chemotherapy showing reduced sperm motility under the light microscope when compared to control specimens from fertile subjects had a lower level of R123 staining and a higher level of EB staining (Evenson et al, manuscript in preparation). These observations suggest that the changes in R123 fluorescence intensity in ejaculated sperm are primarily due to changes in mitochondrial membrane potential rather than mitochondrial number.

The staining intensity of R123 is concentration dependent under equilibrium conditions over a range of 0.2-150 μg/ml; staining at 10 μg/ml used here provides for a strong fluorescent signal. The uptake of the dye is rapid, reaching a plateau by 10 min; after transfer of the cells to dye-free media a new equilibrium is reached by 30 min and remains stable for at least 1 hour.

These data and studies of other patients with known fertility problems show high correlation between motility of sperm by light microscopy and intensity of R123 staining.

This new technique for simultaneously quantitating sperm "motility" and viability by flow cytometry offers objective measurements based on large numbers of cells per sample. These measurements alone or in combination with the methods recently described by us Evenson et al, Science 210:131 (1980) correlating fertility with nuclear chromatin resistance to denaturation in situ, demonstrate the usefulness of flow cytometry in the fertility clinic.

Figure 2:
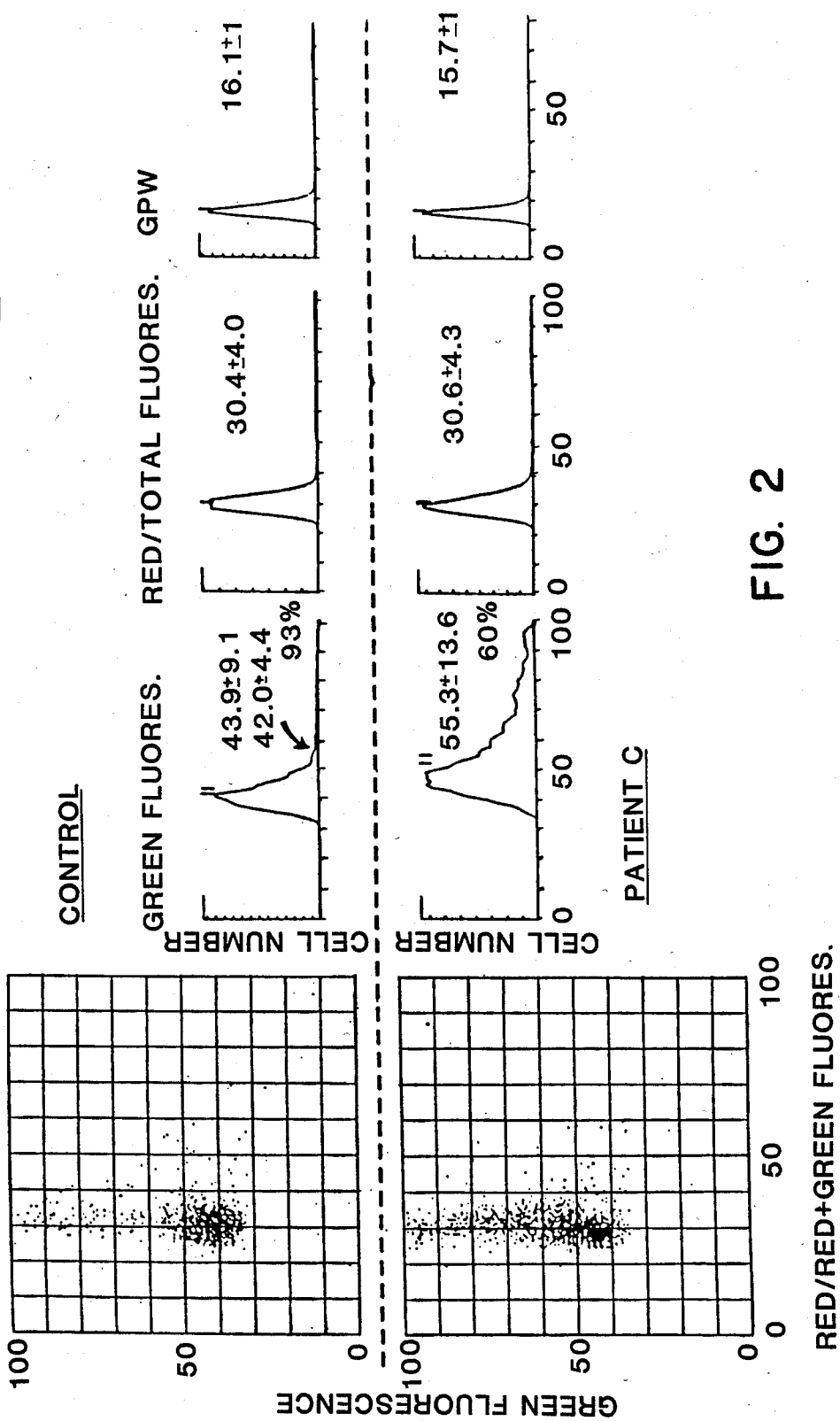
FIG. 2 shows a comparison of acridine orange (AO) stained semen cells from a control, with those from a patient newly diagnosed as having Hodgkin's disease, and before therapy.

FIG. 2 shows data from patient C reflecting semen stained with AO.

The data to the right of each scatplot are computer generated frequency histograms of green fluorescence, red/total fluorescence, and green pulse width (gpw).

The significant difference between these two samples is the increased green fluorescence of the semen cells obtained from the patient. The mean total green fluorescence for the control is $43.9 \pm 9.1$ while that of the patient is $55.3 \pm 13.6$. The mean green fluorescence of the population selected below channel 58 in the normal control (see arrow on control green fluorescent frequency histogram) is $42.0 \pm 4.4$; 93% of the cells from the control are within three standard deviations ($42.0 \pm 13.2$) of this mean while only 60% of the cells from the patient are within 3 standard deviations of this mean. It is clear that more sites are available for AO intercalation in the patient sperm suggesting that his sperm chromatin is not normally condensed. Note from the scatplot and the frequency histogram that the mean red/total fluorescence value of the control ($30.4 \pm 4.0$) is nearly the same as the patient ($30.6 \pm 4.3$) indicating no significant difference in single strand nucleic acid stainability. Likewise, little difference is seen in mean green pulse width (gpw) values ($15.1 \pm 1.9$ vs. $15.7 \pm 1.6$) indicating no significant difference in cell size/shape, which was confirmed by light microscopy. This increased green fluorescence is often seen in samples from cancer patients (pre- and post therapy) as well as in patients attending an infertility clinic.

CONCLUSION

Conventional semen analysis typically includes a light microscopic assessment of sperm numbers, motility and morphology. These measurements are relatively time consuming and lack good statistical significance. Furthermore, it is difficult to identify various sperm precursor cells and somatic cell sometimes present in semen.

The methods described here offer significant advantages for analysis of cell types, maturation level of sperm chromatin structure and sperm count. These advantages include rapidity of analysis of a large number of cells, providing statistical strength and precise quantitation of amounts and/or structure of nucleic acids. Although rapidity of measurement is important, the most significant aspect of this method is the ability to quantitate parameters of immaturity and/or abnormality of the sperm nuclear chromatin that is not possible by light microscopy. Furthermore, in the case of patients with diminished gonadal function, for example, during and post-chemotherapy or radiotherapy for cancer, we have classified some semen samples as azoospermatic by light microscopy analysis yet the flow cytometry methods permit detection and analysis of small numbers of sperm (eg. 100— in the ejaculate). This may prove important since some patients (e.g. post chemotherapy) having a very low sperm count have flow cytometry analysis within normal limits. Studies presently underway will indicate whether this is of prognostic value.

The relationship between increased levels of $F_{530}$ staining in sperm and chromatin structure is not clear as yet. Current electron microscope studies (Evenson, to be published) suggest that the chromatin is not as condensed in sperm with increased $F_{530}$ staining as in normal, fertile controls. The relationship between chromatin condensation and fertility is unclear also since it is not known whether sperm with less condensed chromatin are on average less likely to successfully fertilize ova. In this context, however, other studies in this laboratory have shown a relationship between chromatin structure and fertility, i.e. sperm nuclear DNA is less resistant to thermal denaturation in situ in cases of subfertility. Current work also suggests that sperm demonstrating increased $F_{530}$ stainability have increased thermal denaturation of the DNA in situ. However, thermal denaturation is the more sensitive technique for detection of alterations in chromatin structure that may be related to fertility. Cases of questionable fertility in humans and bulls have been observed despite normal sperm count, motility index and morphology by both classical light microscope methods and FCM analysis of AO stained semen aliquots; however, following thermal stress of the isolated nuclei (7) the DNA denatures easily indicating an abnormality of chromatin structure.

Major criteria for clinical evaluation of semen samples include: (1) sperm number, (2) sperm viability, (3) sperm motility, (4) sperm morphology/maturation and (5) ratios of cell types. Parameters 1-3 can be determined by a single FCM measurement using R123/EB staining and parameters 4 and 5 by a second FCM measurement using AO staining.

What is claimed is:

1. Process for characterizing sperm motility and viability comprising the steps of
   staining a sample of the sperm with Rhodamine 123 and ethidium bromide,
   applying flow cytographic measuring techniques to count, simultaneously, the sperm fluorescence emissions at green frequencies 515-575 nm and at red frequencies 600-650 nm, the green counts being correlated with sperm motility and the red counts being correlated with putative dying or dead cells.

2. Process of claim 1 further comprising
   staining a second sample of the sperm with acridine orange and applying flow cytographic measuring techniques to count, simultaneously, the sperm fluorescence emissions at green frequencies 515-575 nm and at red frequencies 600-650 nm, which counts are correlated with cell type and normality.

* * * * *